United States Patent [19]

Greenhut et al.

[11] Patent Number: 5,480,413
[45] Date of Patent: Jan. 2, 1996

[54] APPARATUS AND METHOD FOR STABILIZING THE VENTRICULAR RATE OF A HEART DURING ATRIAL FIBRILLATION

[75] Inventors: Saul Greenhut, Aurora; Bruce Steinhaus, Parker; Albert Dawson, Littleton; Tibor Nappholz, Englewood, all of Colo.

[73] Assignee: Telectronics Pacing Systems, Inc., Englewood, Colo.

[21] Appl. No.: 347,279

[22] Filed: Nov. 30, 1994

[51] Int. Cl.⁶ ................................. A61N 1/368
[52] U.S. Cl. ................................................. 607/14
[58] Field of Search ............................ 607/9, 10, 11, 607/12, 13, 14, 15, 16, 17, 18, 27, 28, 30–32

[56] References Cited

U.S. PATENT DOCUMENTS 4,998,974  3/1991  Aker .......................... 607/14

FOREIGN PATENT DOCUMENTS

40444/93  11/1992  Australia ....................... 607/9

OTHER PUBLICATIONS

A Quantitative Model for the Ventricular Response During Atrial Fibrillation, Richard J. Cohen, Rronald D. Berger, Theodore E. Dushane, 1983 IEEE, pp. 796–781.

A New Pacing Method for Rapid Regularization and Rate Control in Atrial Fibrillation, Chu–Pak Lau, Wing–Hung Leung, Cheuk–Kit Wong, Yau Ting Tai and Chun–Ho Cheng; May, 1990; vol. 65, pp. 1198–1203.

Effect of Right Ventricular Pacing on Ventricular Rhythm During Atrial Fibrillation; Fred H. M. Wittkampf, Mike J. L. deJongste, Henk I. Lei, Frits L. Meijler; Mar., 1988; The American College of Cardiology, pp. 539–545.

Rate Stabilization by Right Ventricular Pacing in Patients with Atrial Fibrillation; F. H. M. Wittkampf and M. J. L. DeJongste; Nov.–Dec., 1986; PACE, vol. 9, pp. 1147–1153.

*Primary Examiner*—Angela D. Sykes
*Assistant Examiner*—Stephen Huang

[57] ABSTRACT

A pacemaker is provided in which ventricular rate instability is detected and automatically corrected by gradually increasing the ventricular pacing rate. Once the ventricle is stabilized, its pacing rate is gradually decreased as much as possible without losing ventricular stability. Ventricular instability can be a result of an atrial tachyrhythmia such as atrial fibrillation. Therefore, if the pacemaker is a dual chamber pacemaker, its operation is switched to a single chamber pacing mode thereby decoupling the ventricular pacing signals from the atrial pacing signals and atrial triggered ventricular pacing is inhibited until the atrial fibrillation terminates.

13 Claims, 9 Drawing Sheets

APPARATUS AND METHOD FOR STABILIZING THE VENTRICULAR RATE OF A HEART DURING ATRIAL FIBRILLATION

BACKGROUND OF THE INVENTION

A. Field of Invention

The subject invention pertains to pacemakers, and more particularly to a pacemaker with means for stabilizing the ventricular rate, during atrial tachyrhythmia/fibrillation, by pacing the ventricle at successively higher rates until a steady state condition is established for the ventricle.

B. Description of the Invention

One problem experienced by some heart patients is a random depolarization or beat in the atrium, usually referred to as atrial fibrillation. Atrial fibrillation, while uncomfortable, does not constitute an immediate danger, by itself, to the patient and accordingly, the normal clinical approach to such a condition is to ignore it or to treat it in either an inadequate or a drastic manner. However, one indirect result of atrial fibrillation is an irregular ventricular rate. In other words, during atrial fibrillation, the ventricular intervals may vary substantially from one ventricular event to the next. The mechanism for this biological phenomenon is not understood completely. It has been suggested that, during atrial fibrillation, the AV node receives numerous successive stimuli originating from the atrium, and while each stimulus alone has a low amplitude which is insufficient to trigger a ventricular contraction, they do cause partial depolarizations. The effects of these partial depolarizations is cumulative, so that when a sufficient number of such stimuli are received, the AV node is depolarized resulting in unstable random ventricular contractions. (See R. J. Cohen et al, QUANTITATIVE MODEL FOR VENTRICULAR RESPONSE DURING ATRIAL FIBRILLATION, IEEE Transactions on Biomedical Engineering Volume 30, pages 769–782 (1983)). Ventricular instability is undesirable because it is uncomfortable for the patient. Presently, symptomatic patients are treated with drugs which are frequently ineffectual and/or have undesirable side effects or they are treated with AV nodal/ablation, a drastic procedure. However, stabilizing the ventricular rate during atrial fibrillation can lead to improved cardiac output, diastolic blood pressure, pulmonary artery pressure and end diastolic mitral valvular gradient. (C-P Lau, Leung, C-K Wong, Y-T Tai, C-H Cheng. A NEW PACING METHOD FOR RAPID REGULARIZATION OF RATE CONTROL IN ATRIAL FIBRILLATION, Am J Cardiol 65:1198–1203, (1990)).

It has been found that during atrial fibrillation, the ventricle can be stabilized at a rate approximately equal to the average intrinsic ventricular rate. Again, the mechanism of how the ventricle is stabilized by a pacing rate lower than the maximal intrinsic ventricular rate is not completely understood. It has been suggested that ventricular pacing eliminates the spontaneous depolarization phase of the AV node. F. H. M. Wittkampf, M. J. L. DeJongste, RATE STABILIZATION BY RIGHT VENTRICULAR PACING IN PATIENTS WITH ATRIAL FIBRILLATION. PACE 9:1147–1153 (1986). F. H. M. Wittkampf, M. J. L. DeJongste, H. I. Lie, F. L. Meigler. EFFECT OF RIGHT VENTRICULAR PACING ON VENTRICULAR RHYTHM DURING ATRIAL FIBRILLATION, J Am Coll Cardiol 11:539–545, (1988). These articles disclose that the ventricle may be stabilized by using 93–97% of the sensed and paced ventricular depolarizations for pacing. However this method would pace atrial flutter and atrial fibrillation with a regular ventricular response which would not be beneficial and result in overpacing. The proposed method provides a negative feedback (closed-loop control) on pacing and stability, whereas the previous method was open loop.

Another procedure (see Lau, supra) that was investigated to stabilize ventricular instability during atrial fibrillation was to apply an additional stimulus at a preselected interval after every sensed conducted ventricular beat. The average interval was about 230 ms. However it is believed that this procedure is unsatisfactory because it may result in proarrhythmia by pacing the ventricle during the vulnerable period of ventricular repolarization.

OBJECTIVES AND SUMMARY OF THE INVENTION

In view of the above, it is an objective of the present invention to provide a pacemaker which, during extended atrial fibrillation, automatically stabilizes ventricular pacing, to avoid discomfort and to insure a consistent blood flow for the patient.

A further objective is to provide a dual chamber pacemaker, which, in case of atrial fibrillation, automatically decouples ventricular pacing from the atrium and provide antiarrhythmic therapy until the ventricle is stabilized.

Yet another objective is to provide a pacemaker which is capable of automatically stabilizing the ventricle, and once the ventricle is stabilized, to reduce the ventricular pacing to the lowest level at which ventricle remains stable.

Yet a further objective is to provide a single chamber pacemaker which can detect atrial fibrillation and provide automatic antiarrhythmic therapy to the ventricle when atrial fibrillation is detected.

Other objectives and advantages of the invention shall become apparent from the following description of the invention. Briefly, a pacemaker constructed in accordance with this invention includes a pace and sense circuit providing interfacing with the outside world and a digital microprocessor receiving signals from the pace and sense circuit and providing, in response, control signals for cardiac pacing. The microprocessor detects atrial fibrillation and, in response, decouples the ventricular pacing from the atrium and provides stabilizing therapy to the ventricle. More particularly, the microprocessor monitors the ventricle and, if its rate is unstable, it increases the ventricular pacing rate until the ventricle stabilizes. Once the ventricular rate stabilization is achieved, the microprocessor attempts to decrease the ventricular pacing rate while still maintaining stabilization.

In a dual chamber pacemaker operating in a DDD, DDDR, VDD or VDDR model, a monitor is provided, preferably implemented as software in the microprocessor, which monitors the atrial electrical activity to detect atrial tachyarrhythmias. When an atrial tachyarrhythmia is detected, the pacemaker is switched to single chamber (ventricle) pacing and, if necessary, the ventricle is stabilized as discussed above. When the atrial tachyarrhythmia ceases, the pacemaker resumes dual chamber operation.

In a single chamber ventricular pacemaker, atrial fibrillation is detected by other means, such as by monitoring the R-to-R wave interval variability. If this variability suddenly increases above an average value generated over a preselected number of past intervals, then atrial fibrillation is assumed. Alternatively, a measure of absolute variability and threshold can also be used for this purpose. Another means of detecting atrial fibrillation is to compare the intrinsic ventricular rate to a metabolic indicated rate, which is dependent on the actual cardiac demand. If the intrinsic pacing and metabolic indicated rate track each other, the patient is probably involved in an exercise which requires an increased cardiac output. However, if an intrinsic ventricular rate substantially exceeds the metabolic indicated rate, it is assumed that a tachy-arrhythmia is present, provided the patient does not suffer from ventricular tachyarrhymias.

DETAILED DESCRIPTION OF THE INVENTION

Figure 1:
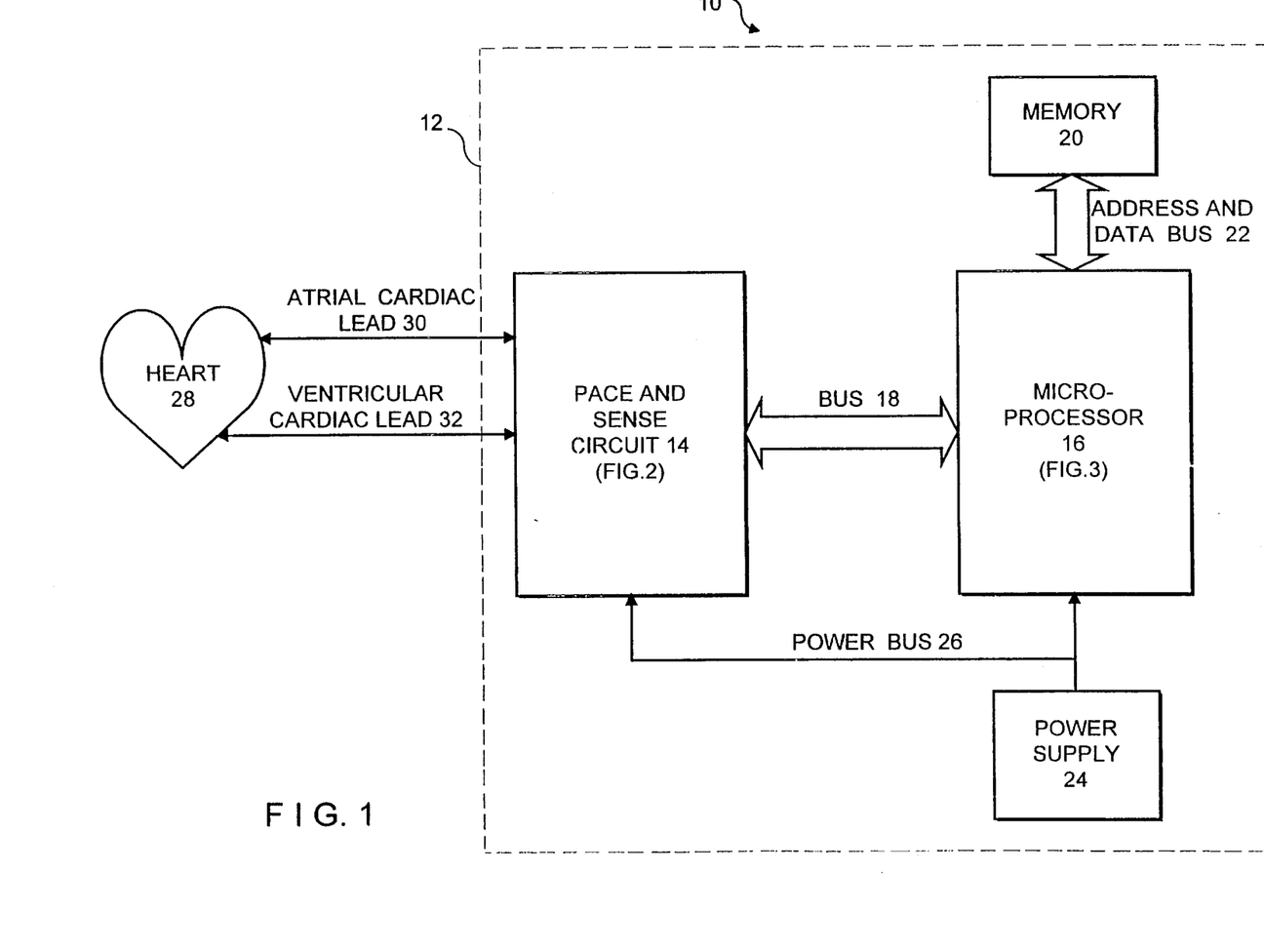
FIG. 1 shows a block diagram of a pacemaker constructed in accordance with this invention.

Referring now to FIG. 1, a pacemaker 10 constructed in accordance with this invention includes an implantable housing 12. The housing holds a pace and sense circuit 14, described in more detail in FIG. 2, and a microprocessor 16, described in more detail in FIG. 3. The pace and sense circuit 14 and the microprocessor 16 are interconnected by a bus 18 for exchanging data, as well as communication and control signals. The pacemaker 10 further includes a memory 20 connected to the microprocessor 16 by a data and address bus 22, and a power supply 24 providing power to the various components of pacemaker 10 via power bus 26.

Once implanted, the pacemaker 10 is connected to a patient's heart 28 by two leads 30, 32. Preferably, these leads 30, 32 are bi-polar leads with lead 30 being connected to the atrial chamber of the heart, and lead 32 being connected to the ventricular chamber. Therefore leads 30 and 32 are known as the atrial cardiac lead and the ventricular cardiac lead, respectively. It should be understood that the arrangement of the pacemaker 10 and leads 30 and 32 do not form a part of this invention. Other arrangements may be used as well, using other types of leads including tri-polar leads, unipolar leads and so on. In some embodiments, lead 30 may be absent or may only sense (not pace). For example, in VDD mode lead 30 may be used as a "single-pass" lead.

Figure 2:
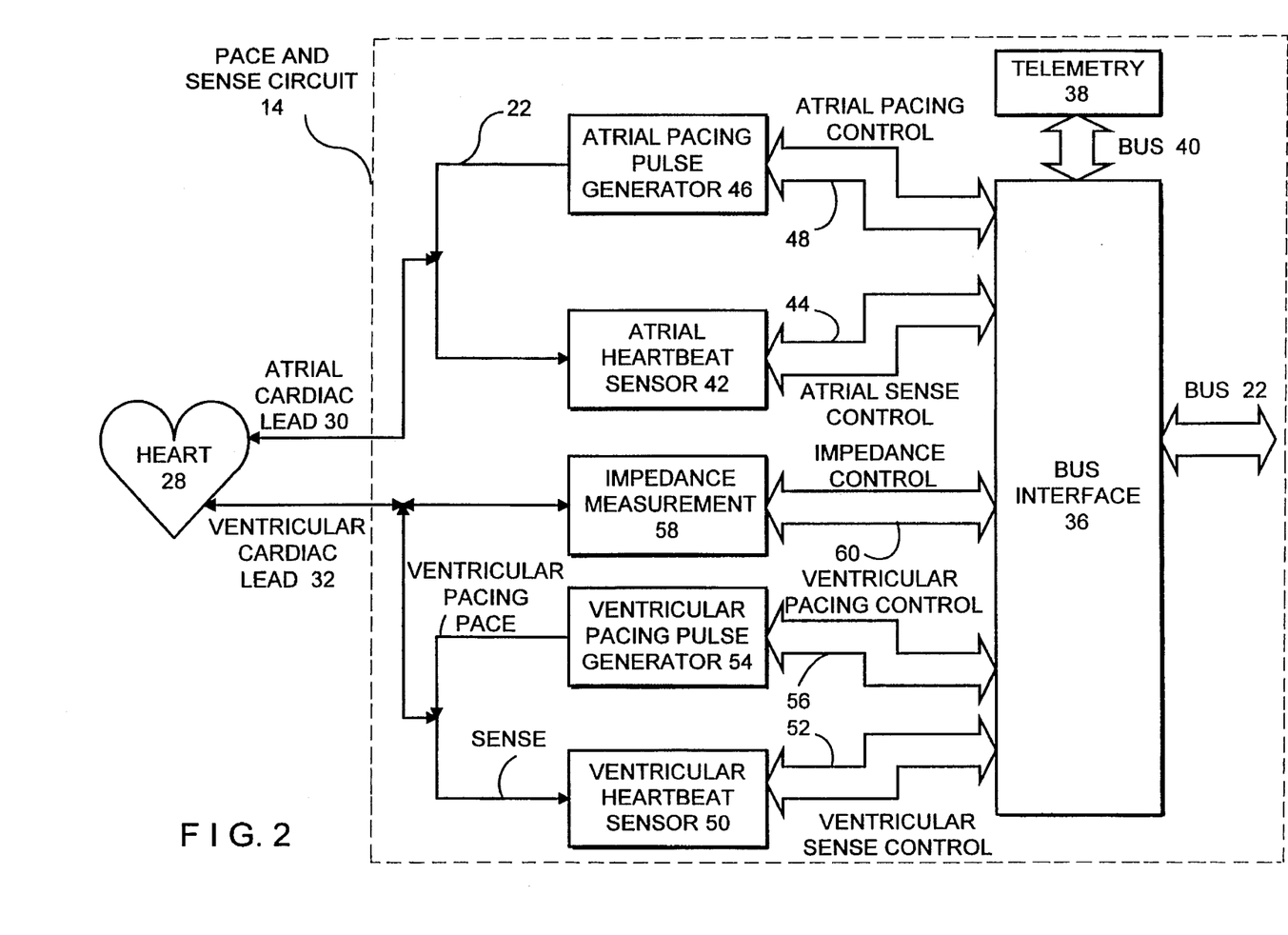
FIG. 2 shows a block diagram for the pace and sense circuit for the pacemaker of FIG. 1.

Referring now to FIG. 2, the pace and sense control circuit 14 includes a bus interface 36, a telemetry circuit 38 and various other sensing and control circuits for sensing the status of the chambers of heart 28 and to provide appropriate pacing signals thereto. The bus interface 36 provides interfacing with microprocessor 16 via bus 18. The telemetry circuit 38 provides communication with the outside world by, for example, RF. Signals with the telemetry circuit are exchanged via telemetering bus 40.

More specifically, signals from the atrium are sensed through lead 30 by the atrial heartbeat sensor 42. This sensor 42 is controlled by the atrial sense control bus 44. Atrial pacing pulses are generated for lead 30 by atrial pacing pulse generator 46. This generator is controlled by the atrial pacing control bus 48. Similarly, the ventricular chamber is sensed through lead 32 by ventricular heartbeat sensor 50, which is controlled by a ventricular sense control bus 52. Pacing pulses for the ventricular chamber are generated by the ventricular pacing pulse generator 54, controlled by the ventricular pacing control bus 56.

In addition, the impedance of the heart tissues are measured through one of the cardiac leads, such as lead 32, by impedance measurement circuit 58. This circuit is controlled by impedance control bus 60. All the control buses are interconnected between their respective circuits and the bus interface 36 to provide two way communication with the microprocessor 16.

Figure 3:
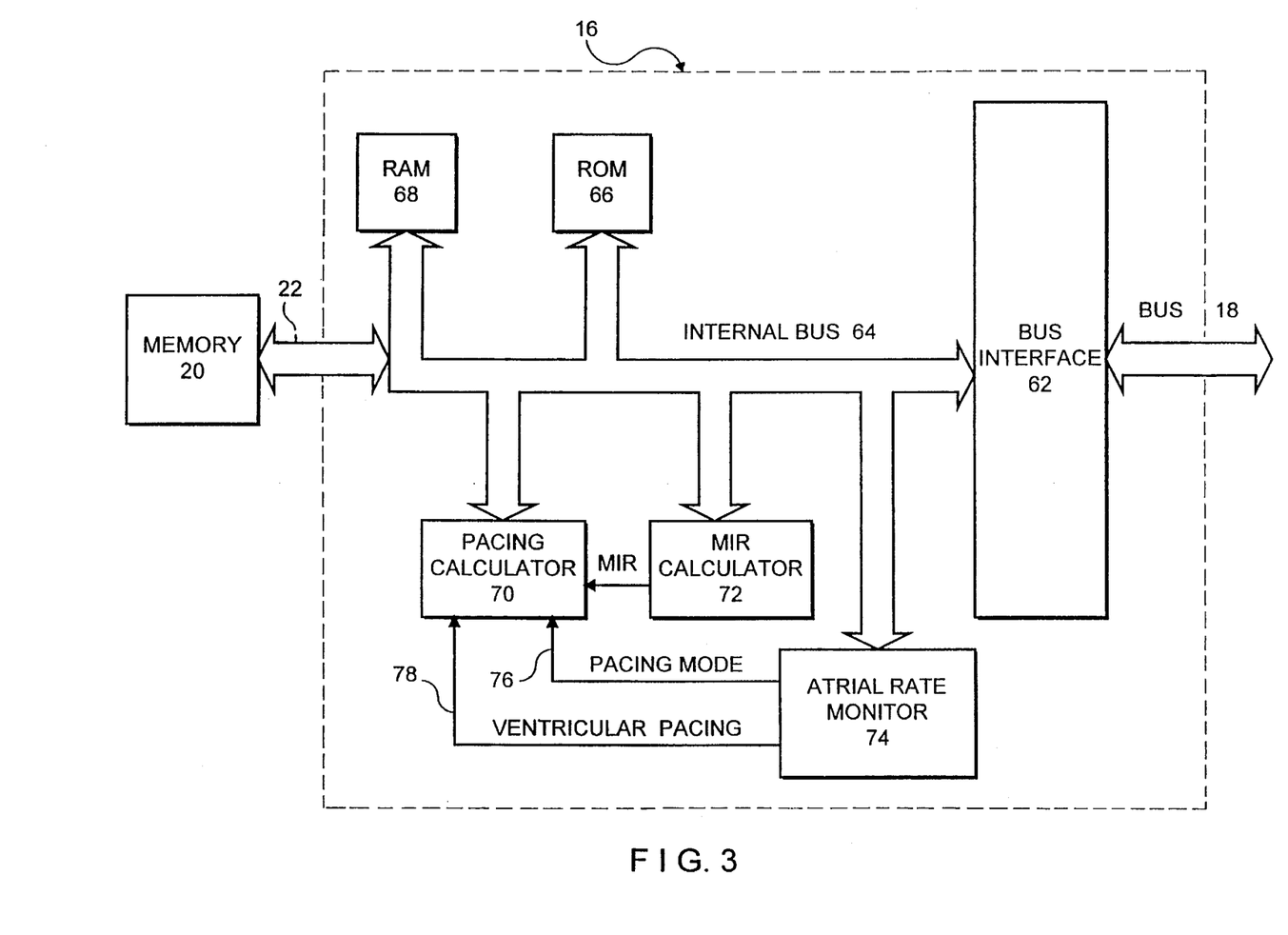
FIG. 3 shows a block diagram for the microprocessor of FIG. 1.

Referring now to FIG. 3, the microprocessor 16 includes a bus interface circuit 62 for interfacing with bus 18, and an internal bus 64 interconnecting the various components of the microprocessor 16. The microprocessor 16 further includes a read only memory (ROM) 66 used for storing programming information, a random access memory (RAM) 68 used as a scratch pad, a pacing calculator 70, a metabolic indicated rate (MIR) calculator 72, and an atrial rate monitor 74.

Except as noted below, the operation of the pacemaker 10 illustrated in FIGS. 1–3 is described in commonly assigned copending application Ser. No. 226,654, Filed on Apr. 12, 1994 by T. A. Nappholz, entitled FORCED ATRIO-VENTRICULAR SYNCHRONY DUAL CHAMBER PACEMAKER, and incorporated herein by reference. Briefly, the impedance of the tissues of the heart 28 is measured by impedance measurement circuit 58 at regular intervals. These sequential measurements are transmitted via control bus 60, bus 18 and internal bus 64 (through the interface circuits 36 and 62) to the MIR calculator 72. This calculator 72 converts these impedance measurements into a minute volume corresponding to the patient's metabolic oxygen demand. Of course, any other Rate Responsive Sensor could be used for the purposes of this application. This minute volume is in turn transformed into a metabolic indicated rate (MIR) and transmitted to the pacing calculator 70. The pacing calculator 70 also receives information regarding the sensing and/or pacing of the atrial and/or ventricular chambers of heart 28 through the respective sensors 42, 50. Based on the received information, the calculator 70 generates pacing control signals for pacing the heart in a particular mode. These control signals are transmitted to the pacing pulse generators 46 and 54 which in response generate appropriate pacing pulses to the ventricle and atrium as described above.

The operation of the microprocessor 16 for correcting the ventricular response to atrial tachyarrhythmias shall now be described in conjunction with the flow chart of FIG. 4. Initially, in step S100, the microprocessor 16 operates the pacemaker 10 in a standard pacing mode such as DDDX (i.e. DDD or DDDR) or VDDX (i.e. VDD or VDDR). As part of this mode of operation, the atrial rate is monitored by monitor 74 through sensor 42 and/or 58 to detect atrial tachyarrhythmias such as fibrillation (AF). This may be accomplished by various methods including comparing the atrial rate to a threshold level, using waveform morphology, or a hemodynamic parameter, or comparison between the metabolic indicated rate (MIR) and the intrinsic atrial and/or ventricular rates. If an atrial fibrillation is detected by monitor 74, the microprocessor 16 enters into a ventriclar rate stabilization mode. In this mode, in step S104, the monitor 74 sends a signal on line 76 to the pacing calculator 70 to reset the pacing to a different mode, such as DDIX or VDIX. Next, in step S106, the monitor 74 selects a new ventricular pacing rate as described more fully below and sends this new rate on line 78 to the pacing calculator 70.

In step S108, the monitor 74 determines whether the ventricular rate for all is stabilized. If the ventricular rate is not stabilized, the monitor reverts to step S106.

Ventricular rate stability can be found using a number of different methods. For example the interval between two R waves (standard in the pacemaker field) can be measured and the stability of this parameter may be defined in terms of statistical variance, standard deviation, rate mean squared difference, normalized mean absolute deviation, normalized approximate interquartile range, autocorrelation, Markov chains, coefficient of variation, histograms, using maximum, average, and minimum values stored in a look-up table, or a normalized mean absolute difference, discussed below.

Steps S106 and S108 are repeated until an optimum ventricular pacing rate is found for which the ventricle is stabilized.

After this optimum rate is found, the microprocessor 16 continues to operate in the mode selected in step S104 at the ventricular rate defined in step S106. As indicated in step S110 the monitor 74 continues to monitor the atrium to determine when the atrial tachyrhythmia has terminated. This function is not sequenced with others but is always on. When the atrial tachyrhythmia is no longer detected, monitor 74 orders the calculator 70 to switch back to the original mode (Step 112) and this original mode of operation is resumed in step S100.

As previously mentioned, the stability of the ventricle can be established using a number of different methods. One method which is particularly advantageous is a so-called normalized mean absolute difference method described in detail below. This method is preferred because it is not very complex and hence can be easily implemented, and yet it has the ability to discriminate ventricular stability.

Briefly, as part of this method, the sequential intervals RR are first measured between adjacent R waves sensed in the ventricle. After i such intervals are measured and assigned sequential designations $RR_1, RR_2, RR_3, \ldots RR_i$, the mean absolute difference parameter MADIFF is calculated using the formula:

$$MADIFF = \left[ \sum_{i=0}^{N} |RR_{(i+1)} - RR_i| \right] / \left[ \sum_{i=1}^{N} RR_i \right]$$

The numerator of this expression is obtained by taking the difference between adjacent $RR_i$ intervals and summing N of these differences. The denominator of this expression is obtained by adding N adjacent intervals $RR_i$. Dividing the sum of the differences by the sum of the intervals results in a parameter MADIFF, which is a normalized mean value for N intervals. This value MADIFF indicates the average variation of the intervals from an average interval after N intervals have taken place.

The parameter MADIFF is then compared to a preset threshold value. This threshold level may be for example 0.1 or 10%. A parameter value MADIFF which exceeds this threshold level is indicative of ventricular activity which is random and unstable. Therefore, the pacing rate is increased by a small amount D1 from the pacing rate used just prior to the detection of AF. D1, for example, may be 5 ppm. The whole process is repeated with this new pacing rate until a pacing rate is achieved for which the MADIFF parameter is below the threshold, indicating that the ventricle has stabilized. Pacing of the ventricle continues with calculated ventricular at the last pacing rate.

It is preferable to pace the ventricle at the lowest rate possible while still maintaining ventricular rate stability. Because the patient's condition may change (i.e. lower level of catecholima), it has been observed that ventricular rate stability is subject to a hysteresis effect. Therefore, after ventricular rate stability is achieved at a higher rate, it is possible to decrease the rate and still maintain stability. Hence, after stability has been achieved, the parameter MADIFF can be adjusted further for successive intervals i. After a predetermined number of intervals have passed, during which the ventricle has remained stable, a new pace rate may be set, for example, by lowering the old pace rate by a preset amount D2. D2 may be, for example, 5 ppm. If in the next N intervals, the ventricle remains stable, the new pacing rate is maintained. Otherwise, the pacing rate is increased by amount D2 and the calculation is repeated for the next N intervals until the ventricle is stabilized again.

The method described above can be implemented as shown in FIGS. 5A and 5B. Starting with FIG. 5A, step S200 is performed after a pathological atrial tachyrhythmia has been detected and the pacemaker has been switched to a new pacing mode as shown in FIG. 4, step S104. In step 200, the variable StR indicates the current pacing rate and initially is set to either the ventricular stability rate (non-R modes) or MIR (R modes). Variable K is set to zero. The variable StR is adjusted up and down, as set forth below, until the lowest pacing rate is found at which the ventricle is stable. The variable K is used to count the number of intervals during which the ventricle is stable. In step 202 the variables i, $RR_d$, and $RR_t$ are set to zero. Variable i is the variable used to count the number of intervals $RR_i$, the variable $RR_d$ is used for the sum of the absolute differences $RR_{i+1} - RR_i$ and the variable $RR_t$ is used to calculate the sum of the intervals $RR_i$ as i progresses from 0 to N.

Steps S204 and S206 are shown as occurring sequentially but in fact they are performed together. In step S206 the interval $RR_i$ is measured. This step is accomplished, by first detecting an R wave and, then, waiting for the next R wave to occur. During this waiting time, the condition of the atrium is monitored in step S204 and if the atrial tachyrhythmia ceases, the microprocessor cycles back to step S112 in FIG. 4.

Figure 5A:
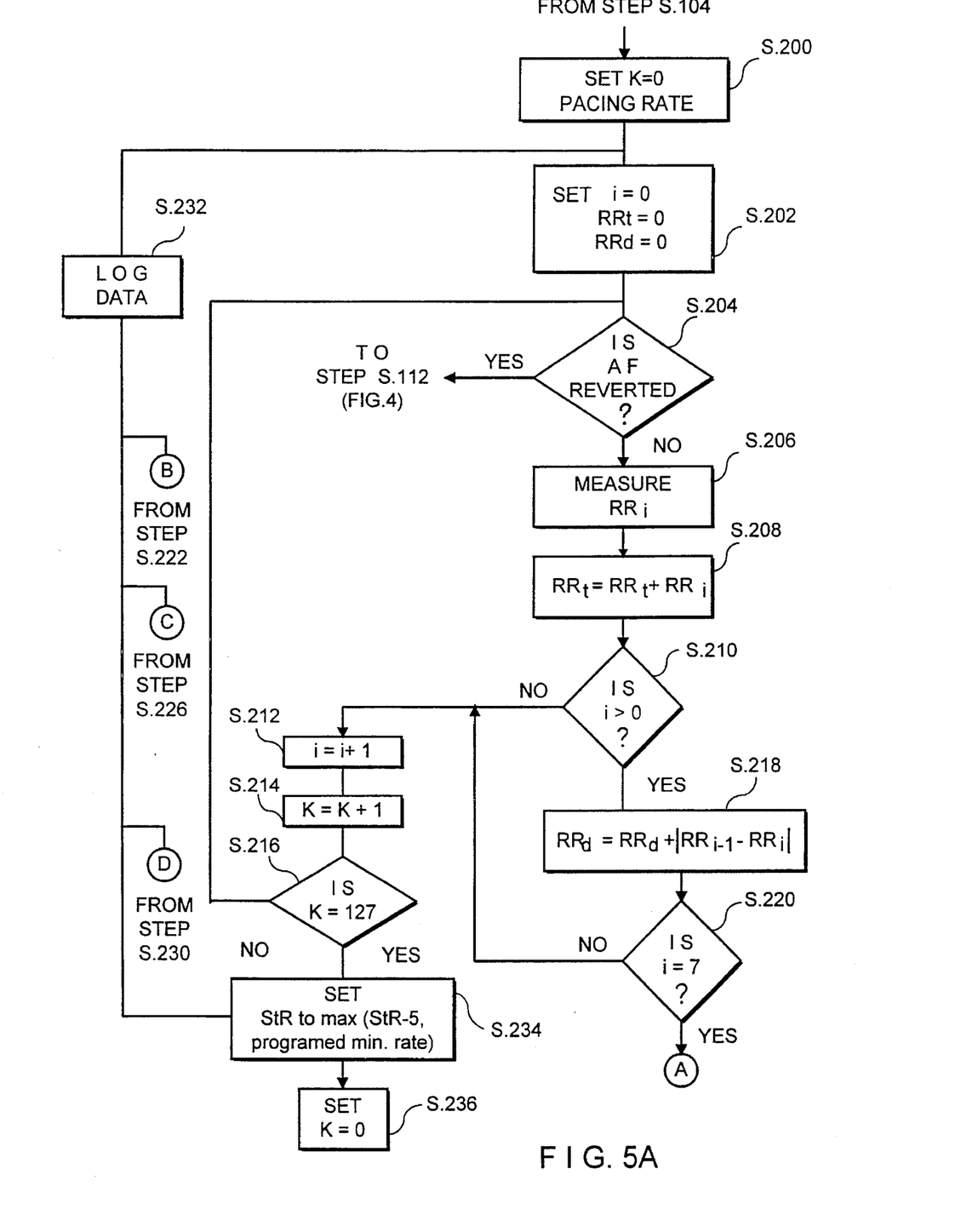
FIGS. 5A and 5B show a flow chart for a preferred embodiment of the invention.

Once an interval $RR_i$ is determined, the microprocessor proceeds to step S208 where this interval $RR_i$ is added to the previous value of $RR_t$ thereby updating the latter. In step S210 a check is performed to determine if interval $RR_i$ is the first interval of a series of N intervals that has been measured. The reason for this check is that for the first interval $RR_0$ there is no difference $RR_d$ to be calculated.

If i=0, then in steps S212 and S214 the variables i and K are incremented. In step S216 a check is performed to see if K has reached a predetermined value, such as 127. If K has not reached this value, the microprocessor cycles back to step 204 and the next measurement $RR_1$ is obtained.

After the second measurement $RR_1$ is obtained, since i>0, the microprocessor cycles from step S210 to step 218 where the difference variable $RR_d$ is updated. In the following step S220, a check is performed to determine if a predetermined number of intervals, such as 8 in FIG. 5A, have been measured. If not, then the microprocessor cycles back to step S212 for incrementing i and K and measuring the next $RR_i$.

Figure 5B:
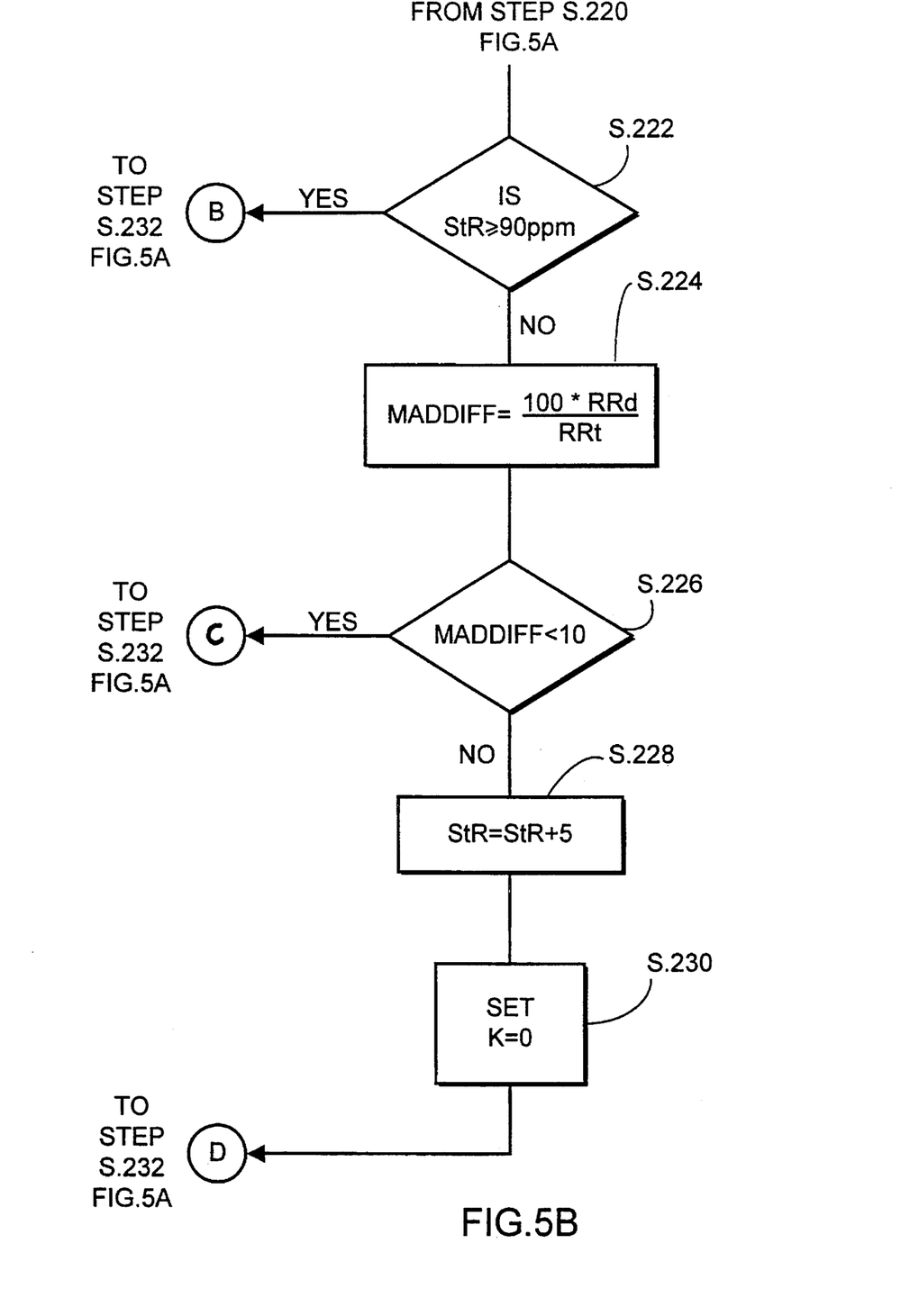

The embodiment of FIGS. 5A and 5B is designed for stabilizing the ventricle of a person at rest. After the preset number of intervals $RR_i$ have been measured (8 in FIG. 5A), the microprocessor proceeds to step S222 (FIG. 5B). In this step, a check is performed to determine if the current pacing rate StR exceeds a preset threshold such as 90 ppm. The purpose of this check is to insure that the rate StR does not exceed this threshold. The threshold of 90 ppm has been selected because it is believed that it is a safe upper limit for pacing a person at rest.

After the check in step S222, in step S224 the parameter MADIFF is calculated as defined above. In the following step S226 a check is made to determine if the parameter MADIFF is below a preset level such as 0.1. As previously discussed, if this parameter is above the preset threshold level, the ventricle pacing is not stable. Therefore in step S228 the pacing rate StR is increased by 5 ppm. In the following step S230, the variable K is reset to zero since, obviously, the ventricle has not been stabilized yet. The microprocessor then cycles to step S232 (FIG. 5A) discussed below.

Importantly, at step S226 if the parameter MADIFF is below the preset threshold (i.e., 0.1), the pace StR is not changed and the variable K is not reset, before cycling to step S232.

Going back to step S216 (FIG. 5A) when a sufficient number of intervals $RR_i$ have been measured without changing the pacing rate StR, i.e., when K reaches 127, the microprocessor proceeds to step S234 where the pacing rate StR is reduced by 5 ppm. In the following step S236, the variable K is reset to zero, and the microprocessor then goes on to step S232.

In step S232, the different variables, such as StR and MADIFF are stored in a memory for future data analysis, if required. The microprocessor then proceeds to step S202 where the whole cycle starts over again.

It should be understood that the various values preset in FIGS. 5A and 5B for the various checks, i.e. in steps S210, S220, and so forth as well as the increments for increasing and decreasing StR are only exemplary and that other values may also be used.

Figure 6:
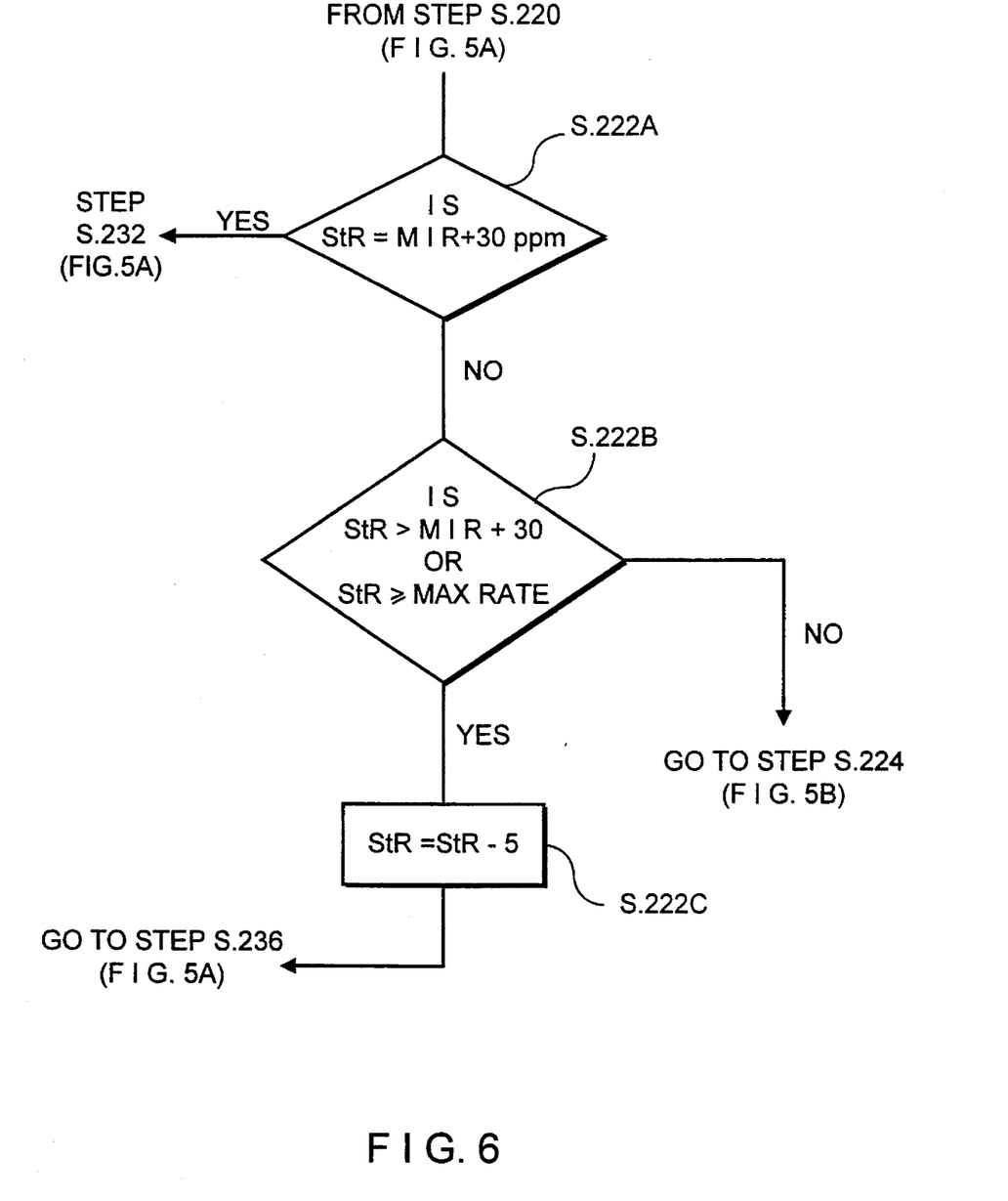
FIG. 6 shows a flow chart for an alternate embodiment of the invention.

As previously described, the embodiment of FIGS. 5A and 5B are designed for a person at rest with a pacing rate limited to 90 ppm. For a person performing some kind of exercise, the embodiment of these Figures may be modified by replacing step S222 (FIG. 5B) with the steps S222A, S222B and S222C shown in FIG. 6. It will be recalled that one of the control parameters used by the pacing calculator 70 in FIG. 3 is a metabolic indicated rate (MIR) derived by calculator 72 (FIG. 3). In FIG. 6, the value of StR is checked to determine if it exceeds the metabolic indicated rate MIR. The metabolic indicated rate is dependant on the physiological demand of the patient's body and hence it is or could be related to other stress level related to the exercise level of the patient. In step S222A a check is performed to see if the current rate StR has exceeded MIR by a preset level such as 30 ppm. If the rate StR has reached this level, then the microprocessor recycles to step S232 without any changes to the rate StR. Step S222B is provided to insure that the rate StR did not somehow exceed either the level set in step S222A (i.e., MIR+30 ppm) or a maximum allowable pacing rate MAXRATE set for the patient. If the rate StR has exceeded these limits, then in step S222C the rate StR is decreased by 5 ppm and the microprocessor returns to step S236 (FIG. 5A). If the rate StR does not exceed the limits of step S222B then the microprocessor goes on to step S224 in FIG. 5B for calculating the parameter MADIFF. From then on the microprocessor proceeds as discussed above.

In the above-described embodiments, the control parameter used to make a determination about the stability of the ventricular rate is $RR_i$, defined as the interval between two adjacent R waves. Alternatively, the control parameter could be the interval between n R waves where n could be an integer greater than one. In other words, the control parameter is the time interval between two non-adjacent R waves. This alternative may be used to reduce the sensitivity of the apparatus to premature ventricular depolarizations.

Figure 4:
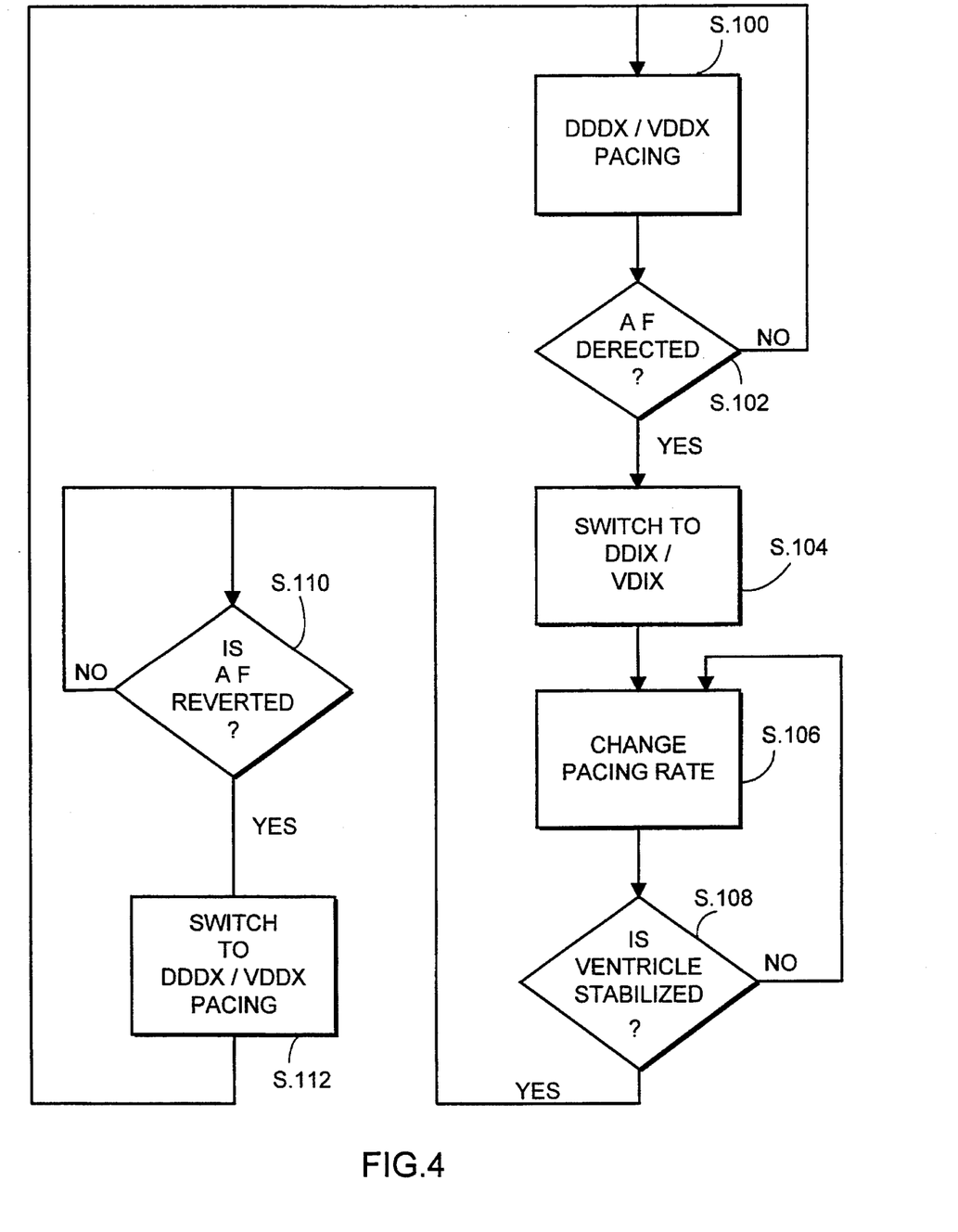
FIG. 4 shows a generalized flow chart for the microprocessor of FIG. 3.

FIGS. 4–6 and the description for these figures pertains to the preferred embodiments of the invention, and more particularly to a method and apparatus for stabilizing the ventricle during atrial fibrillation in association with a dual chamber pacemaker. Of course, the method and apparatus of stabilizing the ventricle can be used for other purposes as well. For example, in FIG. 7, a flow chart is illustrated for a single chamber pacemaker. Initially the pacemaker is operating in a VVIX mode at a pacing rate VR derived from ventricular sensing, as indicated by step S300. In this mode, since atrial sensing is not available, another means must be found to sense atrial fibrillation. For example, the $RR_i$ interval may be measured in step S302. In the following step 304, the parameter MADIFF is determined based on several sequential $RR_i$ measurements in accordance with the procedure set forth above. In step S306 a check is performed to determine if the parameter MADIFF is above a preselected constant C. As previously indicated, the MADIFF parameter provides a quantitative measure of the rate stability of the ventricle. A source of instability of the ventricle is atrial fibrillation. Therefore, the check in step S306 is performed to detect ventricle instability due to the atrial fibrillation. However for this check, the constant C must be larger than in the determination of FIG. 5 step S226, because, for step S226 the assumption can be made that normal sinus rhythm is not present. This assumption cannot be made for step S306. A preferred value of C is about 0.3, i.e. 30% of the average value of RR.

If the calculated value of MADIFF exceeds C, it is assumed that the atrium is undergoing fibrillation, and accordingly in step S308 the rate VR is periodically modified (i.e. incremented by 5 ppm) until the ventricle is stabilized, i.e. the parameter MADIFF falls below 0.1. The process for stabilizing the ventricle is described above, and in the flow chart of FIGS. 5A and 5B.

Figure 7:
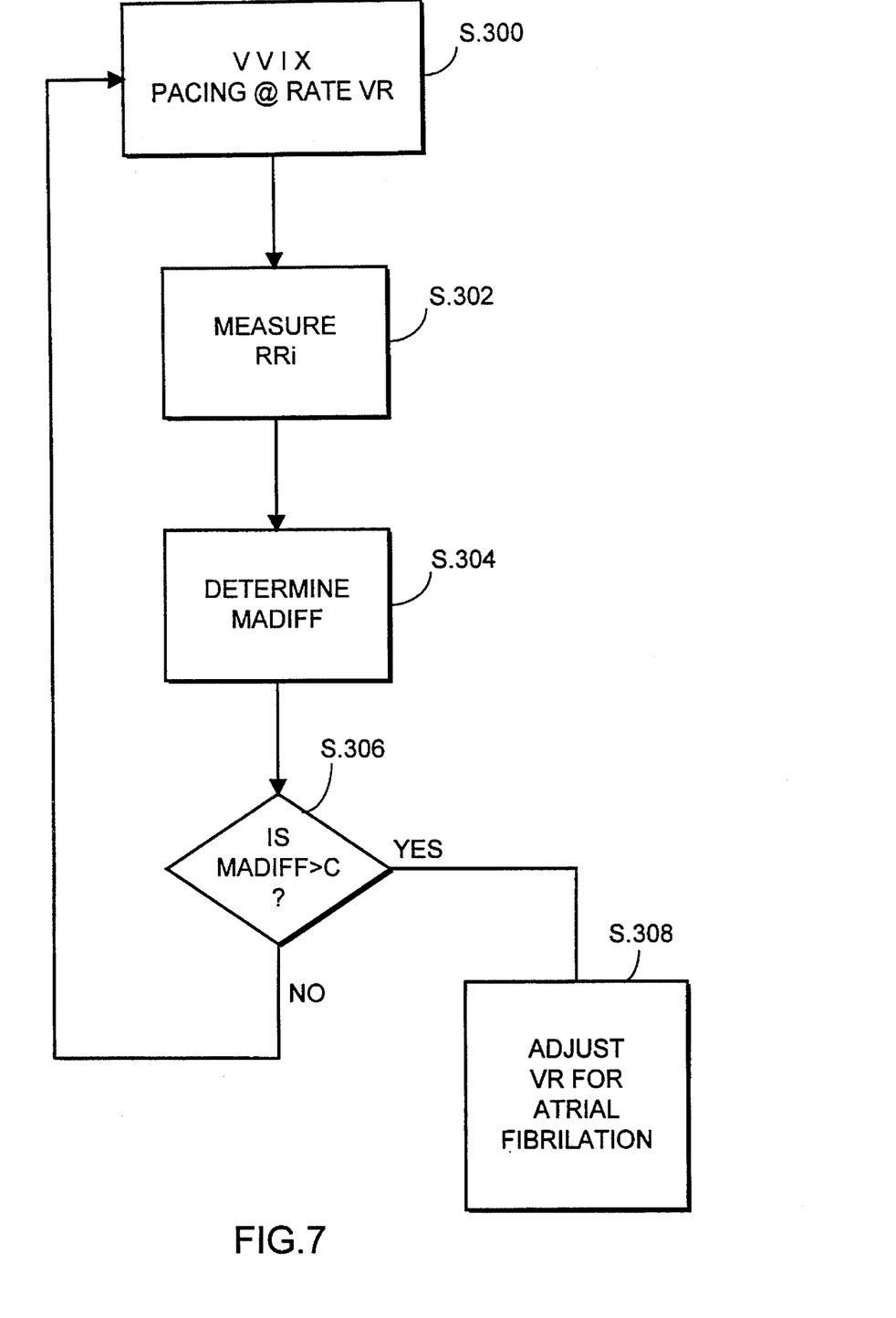
FIG. 7 shows a flow chart for another alternate embodiment for ventricular stabilization in a single chamber ventricular pacemaker.

If, in step S306, the parameter MADIFF is below C, pacing continues at rate VR.

Figure 8:
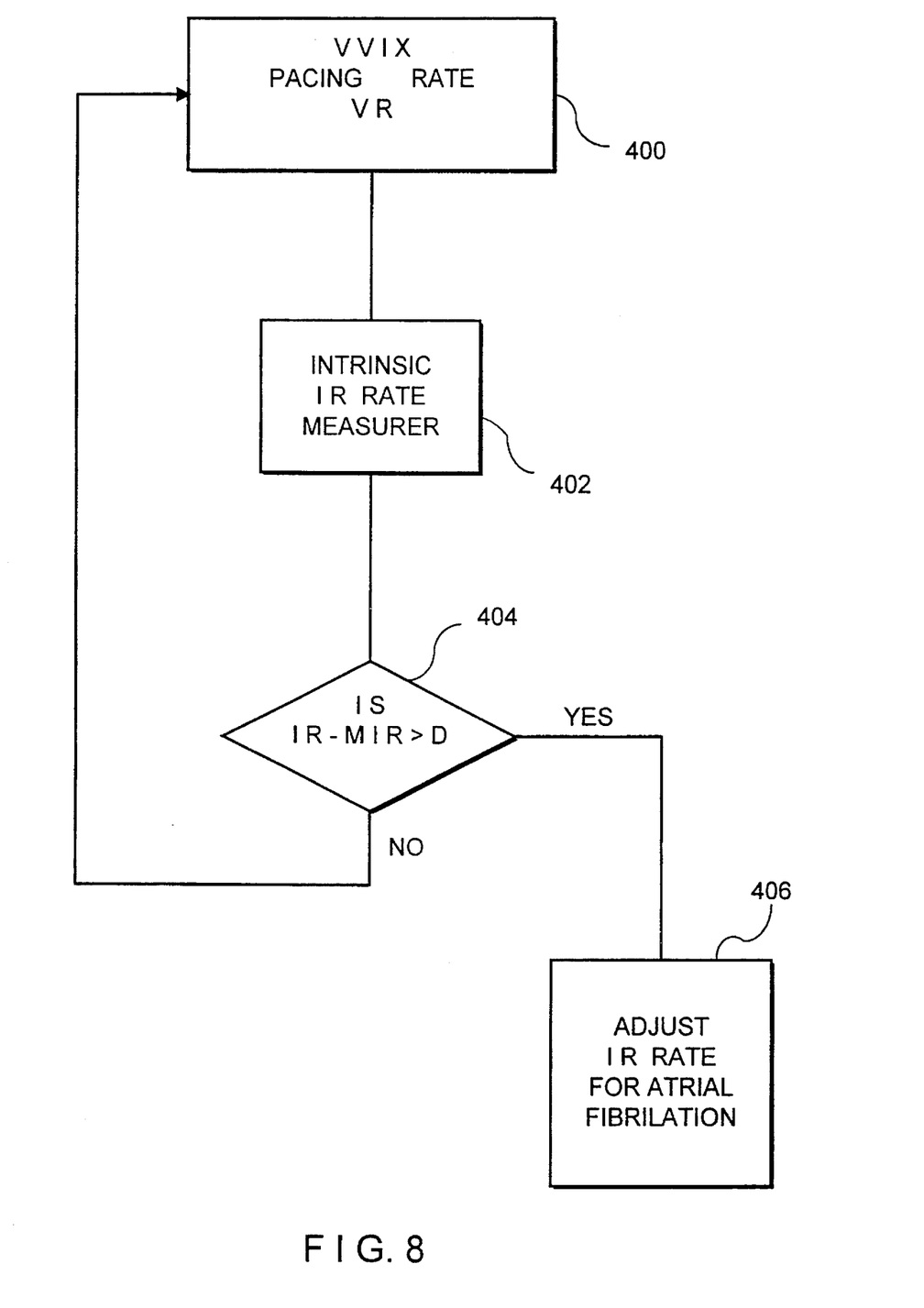
FIG. 8 shows another flow chart for ventricular stabilization with a single ventricular chamber device.

An alternate embodiment to FIG. 7 is shown in FIG. 8. In this Figure, in step S400 the pacemaker is operating in mode VVIX. At regular intervals, the intrinsic rate IR is measured in step S402. This rate is compared to the metabolic indicated rate (MIR) discussed above. The MIR parameter indicates the metabolic demand of the patient's body and therefore it is an accurate representation of the patient's exercise level. If the intrinsic rate (IR) increases while the MIR remains about the same, it is probable that the increase in IR is due to a pathological atrial tachyrhythmia if the patient is not suceptible to ventricular arrhythmias. Therefore, in step S402, if the difference between IR and MIR is greater than a preselected constant D, an atrial tachyrhythmia is assumed and in step S406 the pacing rate is adjusted in accordance with FIG. 7. Constant D may be, for example, 30 ppm. A % change could also be used, such as;

$$100 \times \frac{IR - MIR}{MIR} > E$$

where E is a preselected threshold.

The embodiments of FIGS. 7 and 8 are useful for providing a separate trigger indicative of atrial arrhythmia for example for a patient suffering for paroxysmal episodes of atrial fibrillation. For a patient with chronic atrial fibrillation, the trigger is unnecessary and the pacing rate may be adjusted constantly to eliminate ventricular instability in accordance with the process set forth in FIGS. 4, 5A, 5B.

In patients with a fast ventricular response to AF the electrical therapy described could be combined with a relatively low dose of drug (e.g. beta blocker), so that the ventricular rate for stability during rest is not too high (<90 ppm).

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. An implantable pacemaker for insertion into a patient for stimulating the patient's heart, said pacemaker comprising:

means for detecting R—R intervals between consecutive R-waves in said heart, said R—R intervals defining a ventricular rate in a ventricle of said heart;

means for detecting an atrial tachyrhythmia in an atrium of said heart;

means for determining if said ventricular rate is unstable in response to said atrial tacharrhythmia based on said R—R intervals;

means for pacing said ventricle at a ventricular pacing rate; and means for stabilizing said ventricular rate by increasing said ventricular pacing rate when said ventricular rate is unstable.

2. The pacemaker of claim 1 wherein said means for determining includes means for monitoring a ventricular rate variability, said ventricular rate variability being determined by comparing a predetermined number of R—R intervals to an average R—R interval.

3. The pacemaker of claim 1 further comprising means for decreasing said ventricular pacing rate gradually while maintaining cardiac stability.

4. The pacemaker of claim 1 further comprising means for detecting an atrial fibrillation of said heart.

5. The pacemaker of claim 4 further comprising means for pacing the atrium at an atrial pacing rate, said atrial pacing means being disabled when said atrial fibrillation is detected.

6. The pacemaker of claim 1 wherein said means for detecting said R—R intervals includes means for detecting a plurality of intervals $RR_i$ between R waves, means for determining normalized value for said $RR_i$ and means for determining when said normalized value exceeds a preselected threshold.

7. The pacemaker of claim 1 further comprising means for generating a metabolic indicated rate, said means for determining if said ventricular rate is stable including means for comparing said metabolic indicated rate with said ventricular rate.

8. A pacemaker implantable in a patient for stimulating the heart, said pacemaker comprising:

means for generating atrial induced pacing signals for pacing an atrium;

means for generating ventricular induced pacing signals for pacing a ventricle, in a normal mode of operation, said ventricular induced signals being coupled to said atrial induced pacing signals;

means for detecting R—R intervals between consecutive R-waves in said heart;

means for detecting a ventricular rate instability of a ventricular rate by analyzing said R—R intervals;

means for detecting atrial tachyrhythmia; and means for increasing said ventricular induced pacing signals gradually when said ventricular rate instability is detected until the ventricular rate is stabilized.

9. The pacemaker of claim 8 further comprising means for detecting atrial fibrillation.

10. The pacemaker of claim 9 further comprising decoupling means for decoupling said ventricular induced pacing signals from said atrial induced pacing signals when the atrial fibrillation is detected.

11. The pacemaker of claim 8 wherein said means for detecting R—R intervals includes means for measuring an interval between adjacent ventricular signals and comparing means for comparing said intervals to a threshold level.

12. A method of providing pacing signals to a heart with an implanted pacemaker, said method comprising the steps of:

applying ventricular pacing signals to a ventricle;

monitoring an atrium to determine atrial instability wherein said atrium exhibits random atrial beats by measuring R—R intervals between consecutive R waves in said ventricle; and increasing a rate of said ventricular pacing signals gradually until ventricular rate stability is achieved.

13. The method of claim 10 further comprising the step of decreasing said rate while maintaining ventricular stability.

\* \* \* \* \*